United States Patent [19]

Bryant et al.

[11] Patent Number: 5,183,943
[45] Date of Patent: Feb. 2, 1993

[54] REACTIVATION OF HYDROFORMYLATION CATALYSTS

[75] Inventors: David R. Bryant, South Charleston; James E. Babin, Hurricane; James C. Nicholson, Charleston, all of W. Va.; Donald J. Weintritt, Jr., Houston, Tex.

[73] Assignee: Union Carbide Chemicals & Plastics Technology Corporation, Danbury, Conn.

[21] Appl. No.: 670,874

[22] Filed: Mar. 18, 1991

[51] Int. Cl.$^5$ .............................................. C07C 45/50
[52] U.S. Cl. .................................. 568/454; 568/492; 568/455
[58] Field of Search ........................ 568/492, 454, 455

[56] References Cited

U.S. PATENT DOCUMENTS

| | | | |
|---|---|---|---|
| 3,555,098 | 1/1971 | Olivier et al. | 260/604 |
| 4,292,196 | 9/1981 | Homeier et al. | 568/454 |
| 4,845,306 | 7/1989 | Puckette | 568/454 |
| 4,861,918 | 8/1989 | Miller et al. | 568/454 |

FOREIGN PATENT DOCUMENTS

| | | | |
|---|---|---|---|
| 216315 | 4/1987 | European Pat. Off. | |
| 22571 | 9/1968 | Japan | 568/492 |
| 43-022571 | 9/1968 | Japan | 568/492 |
| 45-010127 | 4/1970 | Japan | |
| 14482 | 5/1976 | Japan | 568/492 |
| 51-014482 | 5/1976 | Japan | 568/492 |
| 56-033040 | 3/1981 | Japan | |
| 1219763 | 1/1971 | United Kingdom | |

OTHER PUBLICATIONS

"Hydroformylation of Alkanes by use of Rhodium Complex Catalysts" by D. Evans et al. in the *J. Chem. Soc. A*, 1968, pp. 3133–3142.

"Reactivation of Rhodium Hydroformylation Catalyst by Treatment with Aqueous Sodium Bicarbonate" by Anonymous in *Research Disclosure*, Nov.211, (1981), p. 393, #21103.

*Primary Examiner*—Werren B. Lone
*Attorney, Agent, or Firm*—R. J. Finnegan

[57] ABSTRACT

A process for improving the catalytic activity of a partially deactivated solubilized rhodium - tertiary organophosphine complex hydroformylation catalyst.

15 Claims, No Drawings

REACTIVATION OF HYDROFORMYLATION CATALYSTS

This invention relates to a process for improving the catalytic activity of solubilized rhodium-tertiary organophosphine complex hyroformylation catalysts which have become partially deactivated due to halide and/or carboxylic acid poisoning.

BACKGROUND OF THE INVENTION

Processes for forming aldehyde products by the hydroformylation reaction of an olefinic compound with carbon monoxide and hydrogen in the presence of a rhodium-tertiary organophosphine complex hydroformylation catalyst are well know in the art. Of particular interest are those hydroformylation reactions designed to produce aldehydes at low pressures, such as disclosed, e.g. in U.S. Pat. Nos. 3,527,809; 4,148,830 and 4,247,486. Due to the value of the rhodium metal, catalyst lifetime and the ability to reactivate partially deactivated catalysts is of vital importance to the success of commercial hydroformylation.

Experience has shown that, extrinsic catalyst poisons such as halide and carboxylic acid compounds deactivate rhodium - tertiary organophosphine complex hydroformylation catalysts. Such loss in catalytic activity is not to be confused with intrinsic deactivation, i.e., the loss in catalytic activity that inevitably occurs over the course of time during continued prolonged hydroformylation even in the absence of extrinsic poisons. Such intrinsic deactivation is believed to be due to the formation of inactive rhodium complex clusters which are somehow caused by the combined effects of the processing conditions employed. Methods, such as disclosed in U.S. Pat. No. 4,861,918, for reversing such intrinsic deactivation have been found to have little or no effect in reversing catalytic deactivation that has been caused by halide and/or carboxylic acid poisoning. Such extrinsic catalyst poisoning is believed due to the formation of inactive halide-rhodium and/or carboxylic acid-rhodium complexes caused by the presence of such halide and/or carboxylic acids in the hydroformylation reaction medium.

Thus, the presence of such extrinsic poisons in the hydroformylation reaction medium is to be avoided, but such may not always be possible. For instance, such halide or carboxylic acid poisons may enter into the hydroformylation reaction medium as a result of being present as an impurity in one of the reactants, e.g., the olefin feed. Unwanted carboxylic acid might also be present as a result of oxidation of the aldehyde and/or aldehyde condensation by-products during hydroformylation or storage of the reaction medium due to air (i.e., oxygen) contamination. Moreover, such poisons may accumulate over time and can eventually cause the activity of the catalyst to decrease to such a point that it is no longer desirable to operate the hydroformylation process and the catalyst will either have to be reactivated or discharged and replaced with fresh catalyst. Accordingly reactivation of such extrinsically poisoned rhodium complex catalysts is highly important to the state of the art.

U.S. Pat. No. 3,555,098 suggests maintaining or improving the rhodium catalytic activity of a hydroformylation reaction by washing all or a portion of a liquid medium containing the catalyst with an aqueous alkaline solution to remove by-product acid, e.g. carboxylic acid, formed during hydroformylation. However, such a method requires numerous further aqueous washes following the alkaline treatment to ensure complete removal of the alkali employed. Even minor amounts of such alkali compounds left behind in the catalyst solution can strongly catalyze the formation of aldehyde condensation by-products during hydroformylation when using the reactivated catalyst solution and such can be highly detrimental to continuous hydroformylation processes.

Accordingly, there is still a need in the art for a simple method that permits restoration of deactivated rhodium activity that has been caused by halide and/or carboxylic acid poisoning without requiring complicated handling or processing procedures and without introducing unduly adverse side reactions.

DISCLOSURE OF THE INVENTION

It has now been discovered that the activity of a solubilized rhodium - tertiary organophosphine complex hydroformylation catalyst that has become partially deactivated as a result of halide and/or carboxylic acid poisoning can be improved by treating said solubilized partially deactivated rhodium - tertiary phosphine complex catalyst with an aqueous solution of a tertiary alkanolamine.

Thus it is an object of this invention to provide a process for improving the catalytic activity of such partially deactivated rhodium-tertiary organophosphine complex hydroformylation catalysts. Other objects and advantages of this invention will become readily apparent from the following description and appended claims.

Accordingly a generic aspect of this invention can be described as a process for improving the catalytic activity of a solubilized rhodium tertiary organophosphine complex hydroformylation catalyst which has become partially deactivated due to halide and/or carboxylic acid poisoning, said process consisting essentially of (1) mixing under non-hydroformylation conditions, an organic liquid medium containing said solubilized partially deactivated rhodium-tertiary organophosphine complex catalyst, with an aqueous solution containing from about 1 to about 25 percent by weight of a tertiary alkanolamine to form a water-soluble salt between said tertiary alkanolamine and said halide and/or carboxylic acid;

(2) allowing the resulting mixture to settle into two distinct liquid phases;

(3) separating the aqueous phase which contains said salt from the organic phase containing the solubilized rhodium-tertiary organophosphine complex hydroformylation catalyst resulting from steps (1) and (2); and (4) washing said non-aqueous organic phase of step (3) with water, and recovering a solubilized rhodium-tertiary organophosphine complex hydroformylation catalyst that is more catalytically active than said partially deactivated rhodium-tertiary organophosphine complex hydroformylation catalyst starting material.

DESCRIPTION OF THE PREFERRED EMBODIMENTS

As noted above the solubilized rhodium-tertiary organophosphine complex catalyst that may be reactivated in accordance with this invention is a hydroformylation catalyst which has become partially deactivated as a result of halide and/or carboxylic acid poisoning. Accordingly, the improved catalytic activity obtained by the process of this invention is the result of reversing that deactivation of the catalyst caused by halide and/or carboxylic acid poisoning as opposed to reversing any deactivation of the catalyst that may have been caused by the above discussed phenomenon known as intrinsic deactivation. The reactivation process of this invention has little or no effect with regard to reversing any such intrinsic deactivation of the catalyst.

Such halide poisons include halogens, i.e., chlorine, bromine, iodine or florine, and halide compounds, which are capable of complexing with the rhodium of the catalyst and thereby deactivating same. The most common halide poison is chlorine. Carboxylic acid poisons, include carboxylic acid compounds such as those that may be formed during the hydroformylation reaction due to undesirable oxidation of the aldehyde products and/or higher boiling aldehyde condensation by-products and which may also complex with the rhodium of the catalyst and thereby deactivate same. The presence of such poisons in the hydroformylation reaction medium may be the result of contaminated reactant feed streams, e.g., halogen in the olefin feed reactant and/or oxygen or halogen contamination of the syn gas feed. However, it is immaterial to the process of this invention as to just how the presence of such halide and/or carboxylic acid has occurred. Rather, it is sufficient for the purpose of this invention to merely deduce that the rhodium-tertiary organophosphine complex hydroformylation catalyst to be treated according to this invention is one which has become partially deactivated as a result of halide and/or carboxylic acid poisoning. Moreover, the extent of such catalytic deactivation (or catalyst activity) of the catalyst starting material to be treated according to this invention may be determined by monitoring the amount of halide and/or carboxylic acid poisons present in the hydroformylation reaction medium and/or comparing the hydroformylation conversion rate to aldehyde product obtained in the presence of such poisoned catalysts to the conversion rate that is obtainable when using a comparable hydroformylation catalyst containing reaction medium that is free of such poisons. For example, it is considered that about one part per million of chloride calculated as free chlorine will inactivate about three parts per million of rhodium calculated as free metal. Thus, it is considered, e.g., that about 10 parts per million of chloride will cause about 30 percent of the active rhodium of a catalyst in a hydroformylation reaction medium containing about 100 parts per million of rhodium to become deactivated.

The solubilized partially deactivated rhodium - tertiary organophosphine complex catalyst contained in the organic liquid medium to be treated in accordance with this invention is preferably any such catalyst complex derived from an essentially non-aqueous hydroformylation process directed to producing aldehydes by hydroformylating an olefinic compound with carbon monoxide and hydrogen in the presence of a solubilized rhodium-tertiary organophosphine complex catalyst and which has become partially deactivated primarily as a result of halide and/or carboxylic acid poisoning. More particularly the preferred solubilized rhodium-tertiary organophosphine complex hydroformylation catalyst employable in this invention is one which has become primarily deactivated as a result of halide and/or carboxylic acid poisoning (i.e., at least over 50 percent of all deactivation of said catalyst has been caused by halide and/or carboxylic acid poisoning), and more preferably is one that has become at least 20 percent and most preferably at least about 30 percent deactivated as a result of such halide and/or carboxylic acid poisoning. Of course it is to be understood that reactivation by the process of this invention of catalysts, which have become deactivated to a lesser degree as a result of such poisons is possible and certainly beneficial. Such benefits however will be proportionately smaller for the economics involved and thus reactivation of such lesser deactivated catalysts is not as recommended as the preferred aspects of this invention.

The solubilized partially deactivated rhodium - tertiary organophosphine complex catalysts that may be reactivated in accordance with this invention can be present in any suitable organic liquid medium which will not unduly adversely affect the basic purpose of this invention. Moreover, since the process of this invention involves mixing the catalyst containing organic liquid medium with an aqueous solution of a tertiary alkanolamine, followed by phase separation of the organic and aqueous liquid layers, it is important that the organic liquid medium starting material be such that said phase separation can be readily and easily accomplished and that emulsion formation between the organic and aqueous liguids be avoided. It has been found that such preferred phase separation may be obtained and the risk of emulsion formation avoided, when the organic liquid medium containing said solubilized partially deactivated catalyst to be treated also contains a suitable concentration of aldehyde. For example, if the densities of the organic and aqueous phases are nearly equal, then there is very little driving force for phase separation. On the other hand, since the density of aldehydes are relatively dissimilar from that of water, as the aldehyde concentration in the organic liquid medium starting material of the process of this invention increases, the ease of phase separation between the organic and aqueous liquid layers also increases. Accordingly, in general, the organic liquid medium starting materials employable in this invention preferably contain at least about 30 percent by weight of aldehyde and more preferably at least about 45 percent by weight of aldehyde. Moreover, such aldehydes preferably correspond to the aldehyde product of the essentially non-aqueous hydroformylation process from whence the more preferred organic liquid medium starting materials of this invention are derived. Accordingly, most preferably, the organic liquid mediums employable in this invention may comprise all or any part of such hydroformylation reaction mediums, and/or all or any part of the liquid catalyst recycle medium of the corresponding hydroformylation process, that also contains the partially deactivated rhodium -tertiary organophosphine complex catalyst to be treated according to the process of this invention along with a suitable amount of the aldehyde product as discussed above.

As pointed out by the above Prior art, methods for hydroformylating olefinic compounds to produce aldehydes with a rhodium - tertiary organophosphine complex catalyst are well known in the art. Thus it should be clear that the particular non-aqueous hydroformylation process for producing aldehydes from an olefinic compound, as well as the reaction conditions and ingredients of said hydroformylation process, which serve as a means for furnishing organic liquid medium starting material of the present invention, are not critical features of the present invention.

In general preferred hydroformylation processes comprise reacting an olefinic compound with carbon monoxide and hydrogen in a reaction vessel and in the presence of a hydroformylation reaction medium comprising aldehyde products, a solubilized rhodium - tertiary organophosphine complex catalyst, free tertiary organophosphine ligand, and higher boiling aldehyde condensation by-products which also help solubilize said catalysts. In continuous hydroformylation reactions aldehyde products are constantly being removed, the rhodium-tertiary organophosphine complex catalyst either remaining in the hydroformylation reaction medium in the reactor as in the case of a gas recycle operation (e.g. U.S. Pat. No. 4,247,486 and a published paper entitled "Oxo Alcohol Plant Debottlenecking Using New Rhodium Technology" by R. M. Tudor (at Manchester, England May 22, 1979) published by the Institution of Chemical Engineers, North Western Branch, Symposium Papers, pp. 6.1 to 6.11, 1979, No. 3), or being recycled back to the reactor after removal of some of the liquid reaction medium from the reactor and separation of aldehyde product therefrom, as in the case of a liquid catalyst recycle operation (e.g. U.S. Pat. No. 4,148,830). Thus the organic liquid medium starting material employable herein may preferably be derived from any such conventional essential non-aqueous hydroformylation process.

Accordingly the organic liquid medium starting materials employable herein preferably contain at least some amount of four different main ingredients or components, i.e., the rhodium-tertiary organophosphine complex hydroformylation catalyst which has become partially deactivated primarily due to halide and/or carboxylic acid poisoning, free tertiary organophosphine ligand, a suitable amount of aldehyde as discussed above, and higher boiling aldehyde condensation by-products, said ingredients preferably corresponding to those employed and/or produced by the hydroformylation process from whence the organic liquid medium starting material may be derived.

Of course it is to be further understood that the organic liquid medium starting materials of this invention can also contain minor amounts of additional ingredients such as those which have either been deliberately employed in the hydroformylation process or formed in situ during said process. Examples of such additional ingredients that can also be present include unreacted olefin starting material, and in situ formed type products, such as unreacted isomerized olefin, hydrogenated olefin (e.g. corresponding saturated hydrocarbons or paraffin by-products); and in situ type alkyl substituted phosphine ligand by-product (such as described e.g. in U.S. Pat. No. 4,260,828).

Accordingly it should be sufficient for the purpose of this invention to understand that whatever compounds are present during the hydroformylation process from which the organic liquid medium starting materials of this invention are derived, may also be correspondingly present in said organic liquid medium starting materials of this invention.

Thus the particular partially deactivated, poisoned rhodium tertiary organophosphine complex hydroformylation catalyst, present in the organic liquid medium starting material to be treated in accordance with this invention can be any conventional rhodium hydroformylation catalyst which has become partially deactivated primarily due to halide and/or carboxylic poisoning and has been employed in a hydroformylation reaction. Accordingly the particular partially deactivated, poisoned rhodium-tertiary organophosphine complex hydroformylation catalyst, as well as its amount in a given organic liquid medium starting material of this invention, may obviously correspond to and merely be dependent upon the particular rhodium-tertiary organophosphine complex catalyst employed in and/or formed under the reaction conditions of the particular hydroformylation reaction from whence the organic liquid medium starting material to be treated according to this invention has been derived. For example illustrative rhodium-tertiary organophosphine complex catalysts and hydroformylation reactions, include e.g. those disclosed in U.S. Pat. Nos. 3,527,809; 4,148,830; 4,247,486; 4,283,562; 4,400,548; 4,491,675; 4,593,127; and PCT Application, Publication No. WO 80/01690 (published August, 1980); and the like, the entire disclosures of which are incorporated herein by reference thereto. Of course mixtures of different catalysts and organophosphine ligands can be employed if desired. Moreover, as noted in said references, the hydroformylation processes are generally and preferably carried out in the presence of free tertiary organophosphine ligand i.e. ligand that is not complexed with the rhodium complex catalyst employed. While it is generally preferred that the free ligand be the same as the tertiary organophosphine ligand of the rhodium - tertiary organophosphine complex catalyst, such is not necessary. Accordingly it is to be understood that in the case of the rhodium - tertiary organophosphine complex catalyst, as well as in the case of the free tertiary organophosphine ligand any conventional tertiary organophosphine ligand, heretofore advanced for such hydroformylation purposes, such as disclosed e.g. by the above mentioned references, can be employed herein.

Accordingly illustrative tertiary organophosphines that may be employed, either as the free ligand and/or as the ligand of the rhodium complex catalyst, include e.g. trialkylphosphines, alkyldiarylphosphines, dialkylarylphosphines, dicycloalkylarylphosphines, cycloalkyldiaryl-phosphines, triaralkylphosphines, tricycloalkyl-phosphines, and triarylphosphines, alkyl and/or aryl bisphosphines and bisphosphine mono-oxides, and the like. Of course any of the hydrocarbon radicals of such tertiary organophosphines may be substituted if desired, with any suitable substituent that does not unduly adversely affect the desired result of the process or this invention. Illustrative substituents that may be on the hydrocarbon radicals in addition of course to corresponding hydrocarbon radicals such as alkyl, aryl, aralkyl, alkaryl and cyclohexyl substituents , may include for example silyl radicals such as $-Si(R^9)$ ; amino radicals such as $-N(R^9)_2$; acyl radicals such as $-C(O)R^9$, acyloxy radicals such as $-OC(O)R^9$; amido radicals such as $-CON(R^9)_2$ and $-N(R^9)COR^9$; sulfonyl radicals such as $-SO_2R^9$, alkoxy radicals such as $-OR^9$; thionyl radicals such as $-SR^9$, phosphonyl radicals such as $-P(O)(R^9)$ , as well as, halogen, nitro, cyano, trifluoromethyl, hydroxy radicals, and the like, wherein each $R^9$ individually represents the same or different monovalent hydrocarbon radical having from 1 to 18 carbon atoms (e.g., alkyl, aryl, aralkyl, alkaryl and cyclohexyl radicals), with the proviso that amino substituents such as $-N(R^9)_2$, each $R^9$ taken together can also represent a divalent bridging group that forms a heterocyclic radical with the nitrogen atom, and in amido substituents such as —C(O)N($R^9$) and —N($R^9$)CO$R^9$ each $R^9$ bonded to N can also be hydrogen. Of course it is to be understood that any of the substituted or unsubstituted hydrocarbon radicals groups that make up a particular given tertiary organophosphine may be the same or different.

Such tertiary organophosphines and corresponding rhodium - tertiary organophosphine complex catalysts and/or methods for their preparation are well known as seen e.g. by the above mentioned references. Preferred tertiary organophosphines are triorganophosphines having the formula ($R^{10}$)$_3$P wherein each $R^{10}$ individually represents a monovalent hydrocarbon radical containing from 1 to 18 carbon atoms selected from the alkyl, aralkyl, alkaryl, cycloalkyl and aryl radicals, as disclosed e.g., in U.S. Pat. Nos. 3,527,809 and 4,283,562, and the like.

Among the more preferred tertiary organophosphines are triphenylphosphine, propyldiphenylphosphine, t-butyldiphenylphosphine, n-butyldiphenylphosphine, n-hexyldiphenylphosphine, cyclohexyldiphenylphosphine, dicyclohexylphenylphosphine, tricyclohexylphosphine, tribenzylphosphine, 2,2'-bis(diphenylphosphinomethyl)-1,1'-biphenyl, and the like. The most preferred ligand is triphenylphosphine (TPP), while the most preferred catalyst is a rhodium-TPP complex.

As seen by the above mentioned hydroformylation references, the rhodium complex catalysts are generally considered as consisting essentially of rhodium complexed with carbon monoxide and tertiary organophosphine (generally corresponding to the free tertiary organophosphine ligand also normally present in the reaction medium). The catalyst terminology "consisting essentially of" may include other ligands complexed with the rhodium such as hydrogen in addition to the carbon monoxide and tertiary organophosphine, the hydrogen being derived from the hydrogen gas of the hydroformylation reaction, if not already present in the catalyst precursor. Such hydroformylation catalysts may be formed in situ during the hydroformylation reaction or preformed by methods known in the art. For example preformed rhodium hydridocarbonyl-tris (tertiary organophosphines) may be introduced into the reaction medium of the hydroformylation reaction. Alternatively rhodium catalyst precursors such as rhodium carbonyl tertiary organophosphine acetylacetonates, $Rh_2O_3$, $Rh_4(CO)_{12}$, $Rh_6(CO)_{16}$, $Rh(NO_3)_3$ or rhodium dicarbonyl acetylacetonate, and the like, may be introduced into the reaction medium of the hydroformylation reaction. In any event an active rhodium complex hydroformylation catalyst is present in the hydroformylation reaction medium under the conditions of hydroformylation.

However, it is to be noted that the successful practice of this invention does not depend and is not predicated on any explanation as to the exact structure or nature of the active rhodium complex catalyst species or as to the exact structure or nature of the partially deactivated rhodium hydroformylation catalyst species that may have been formed as a result of such halide and/or carboxylic acid poisoning. Clearly for the purpose of understanding this invention, it is sufficient to simply point out that the partially deactivated rhodium - tertiary organophosphine complex hydroformylation catalysts present in the organic liquid medium starting materials of this invention can be any such rhodium complex hydroformylation catalyst that has become partially deactivated as a result of such halide and/or carboxylic acid poisoning. In general the amount of such partially deactivated rhodium complex catalyst present in the organic liquid medium starting material of this invention preferably corresponds to the amount of the rhodium-tertiary organophosphine complex hydroformylation catalyst employed in the hydroformylation reaction medium of the hydroformylation process from whence the organic liquid medium starting material may be derived, and such amounts are commonly expressed in terms of the amount of rhodium present calculated as rhodium metal. In general, rhodium hydroformylation concentrations ranging from about 25 to about 1500 ppm, calculated as rhodium metal, should be suitable for most purposes, with rhodium concentrations of from about 50 up to 700 ppm, calculated as rhodium metal, being preferred. Of course the organic liquid medium starting materials of this invention may contain higher concentrations of rhodium than present in the hydroformylation reaction medium, and such may be readily obtained e.g. simply by concentrating the rhodium catalyst containing hydroformylation medium prior to employing same as the liquid medium starting material of this invention.

As noted above the tertiary organophosphine ligands defined herein are employed in this invention as both the ligand of the rhodium-tertiary organophosphine complex catalyst as well as, the free tertiary phosphine ligand that is also present in the organic liquid medium starting materials of this invention. In a given situation such rhodium-phosphine complexes and free phosphine ligands of course will correspond to those employed in the hydroformylation process from which said liquid mediums may be derived. In addition, it is to be understood that while the tertiary organophosphine of the rhodium complex catalyst and free tertiary organophosphine ligand present in the reaction medium of a given hydroformylation process are normally the same, different tertiary organophosphine ligands, as well as, mixtures of two or more different tertiary organophosphine ligands may be employed for each individual purpose, if desired. As in the case with the amounts of rhodium complex catalyst employed, the amount of free tertiary organophosphorus ligand present in a given organic liquid medium starting material of this invention will in general correspond to that amount of corresponding free ligand present in the hydroformylation process from which said liquid medium may be derived. For instance, since the hydroformylation process may be carried out in any excess amount of free tertiary organophosphine ligand desired e.g., at least one mole of free tertiary organophosphine ligand per mole of rhodium present in the reaction medium, the amount of free tertiary organophosphine ligand present in a given organic liquid medium starting material of this invention can also be any corresponding excess amount e.g., at least one mole of free tertiary organophosphine ligand per mole of rhodium metal present in the liquid medium starting material.

In general an amount of free tertiary organophosphine ligand of from about 2 to about 300, and preferably from about 5 to about 200 moles per mole of rhodium metal present in the reaction medium should be suitable for most hydroformylation processes. Accordingly, corresponding amounts of free tertiary organophosphine ligand may be present in the organic liquid medium starting materials of this invention.

The organic liquid medium starting materials of this invention also contain higher boiling aldehyde condensation by-products that help serve as solvents for the catalyst and which are formed in situ during the course of the hydroformylation such as described e.g. in U.S. Pat. Nos. 4,148,830; and 4,247,486.

In general such amounts of higher boiling aldehyde condensation by-products in the organic liquid medium starting materials of this invention may range from about 5 to about 70 percent by weight, and more preferably may range from about 5 to about 30 percent by weight based on the total weight of said organic liquid medium starting material. More preferably such amounts of higher boiling aldehyde condensation by-products can correspond to those amounts of such compounds present in the reaction medium or catalyst containing recycle medium of the hydroformylation process from whence the organic liquid medium starting materials of this invention are derived.

Finally as noted above the organic liquid medium starting materials of the process of this invention also preferably contain from about 30 percent by weight, and more preferably from about 45 percent by weight, up to about 95 percent by weight or higher of aldehyde based on the total weight of said organic liquid medium starting material. Said aldehydes preferably correspond to the aldehyde product obtained by the hydroformylation process from whence said organic liquid medium starting materials may be derived. Such aldehydes may contain from 3 to 31 carbon atoms and encompass the corresponding hydroformylation aldehyde products obtained upon hydroformylating olefinic compounds containing from 2 to 30 carbon atoms. Such olefinic compounds can be terminally or internally unsaturated and be of straight-chain, branched chain or cyclic structures, as well as be olefin mixtures, such as obtained from the oligomerization of propene, butene, isobutene, etc., (such as so called dimeric, trimeric or tetrameric propylene, and the like, as disclosed e.g. in U.S. Pat. Nos. 4,518,809 and 4,528,403). Moreover such olefinic compounds may further contain one or more ethylenic unsaturated groups and of course mixtures of two or more different olefinic compounds may be employed as the starting hydroformylation material if desired. Further such olefinic compounds and the corresponding aldehyde products derived therefrom may also contain one or more groups or substituents which do not unduly adversely affect the hydroformylation process or the process of this invention such as described e.g., in U.S. Pat. No. 3,527,809, and the like.

Illustrative olefinic unsaturated compounds are alpha-olefins, internal olefins, alkyl alkenoates, alkenyl alkanoates, alkenyl alkyl ethers, alkenols, and the like e.g., ethylene, propylene, 1-butene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-pentene, 2-hexene, 2-heptene, propylene dimers, propylene trimers, propylene tetramers, 2-ethyl hexene, 2-octene, styrene, 3-phenyl-1-propene, 1,4-hexadiene, 1,7-octadiene, 3-cyclohexyl-1-butene, allyl butyrate, methyl methacrylate, vinyl ethyl ether, vinyl methyl ether, allyl ethyl ether, n-propyl-7-octenoate, 3-butenenitrile, 5-hexenamide, 4-methyl styrene, 4-isopropyl styrene, 4-tert-butyl styrene, alpha-methyl styrene, 4-tert-butyl alpha-methyl styrene, 1,3-diisopropenyl-benzene, eugenol, iso-eugenol, safrole, iso-safrole, anethol, 4-allylanisole, indene, limonene, beta-pinene, dicyclopentadiene, cyclooctadiene, camphene, linalool, and the like.

Accordingly illustrative aldehyde products include e.g, propionaldehyde, n-butyraldehyde, isobutyraldehyde, n-valeraldehyde, 2-methyl-1-butyraldehyde, hexanal, 2-methyl valeraldehyde, heptanal, 2-methyl-1-hexanal, octanal, 2-methyl-1-heptanal, nonanal, 2-methyl-1-octanal, decanal, 2-methyl-1-nonanal, undecanal, 2-methyl-1-decanal, dodecanal, 2-methyl-1-undecanal, tridecanal, 2-methyl-1-tridecanal, pentadecanal, 2-methyl-1-tetradecanal, hexadecanal, 2-methyl-1-pentadecanal, heptadecanal, 2-methyl-1-hexadecanal, octadecanal, 2-methyl-1-heptadecanal, nonadecanal, 2-methyl-1-octadecanal, eicosanal, 2-methyl-1-nonadecanal, heneicosanal, 2-methyl-1-eicosanal, tricosanal, 2-methyl-1-docosanal, tetracosanal, 2-methyl-1-tricosanal, pentacosanal, 2-methyl-1-tetracosanal, heptacosanal, 2-methyl-1-octacosanal, nonacosanal, 2-methyl-1-octacosanal, hentriacontanal, 2-methyl-1-triacontanal, and the like.

Of course it is understood that the aldehyde product of an alpha olefin will normally be a mixture of the normal straight chain aldehyde and its branched chain aldehyde isomer obtained upon hydroformylating said olefin. Moreover, mixtures of totally different aldehyde products can be present in the organic liquid medium starting materials employable in this invention, e.g., when such organic liquid mediums are derived from a process that hydroformylates mixtures of totally different olefinic compounds, such as e.g., mixtures of alpha olefins and internal olefins or mixtures of two different alpha olefins. The preferred aldehyde products present in the hydroformylation reaction product compositions employable in this invention are those derived from hydroformylating alpha olefins, internal olefins and mixtures of such alpha and internal olefins.

The more preferred olefin starting materials are alpha olefins having from 2 to 20 carbon atoms and more preferably from 2 to 14 carbon atoms. Of course it is to be understood that commercial alpha olefins containing 4 or more carbon atoms may contain minor amounts of corresponding internal olefins and/or their corresponding saturated hydrocarbon and that such commercial olefins need not necessarily be purified from same prior to being hydroformylated.

Thus preferably the organic liquid medium starting materials of this invention may correspond to all or a part of the reaction medium of a hydroformylation process as outlined herein, or may correspond to all or a part of the liquid catalyst containing recycle medium of such a hydroformylation process (i.e. that liquid catalyst containing solution obtained, after the removal of a desired amount of aldehyde product from the hydroformylation reaction product medium outside of the hydroformylation reactor or hydroformylation zone) which is recycled to the reactor in order to establish a continuous hydroformylation catalyst recycle process.

Of course it is to be further understood that the organic liquid medium starting materials of this invention may also contain additional ingredients corresponding to those which have either been deliberately employed in the hydroformylation process from which said liquid medium starting materials may be derived or which have been formed in situ during the hydroformylation process. For instance, obviously since an olefin starting material is being hydroformylated, the liquid medium starting materials of this invention may contain some unreacted olefin starting material. In general amounts of unreacted olefin may range from 0 to about 20 percent by weight of the organic liquid medium starting material.

Likewise, minor amounts of in situ type by-products that may be formed during the hydroformylation process may also be correspondingly present in the liquid medium starting materials of this invention, e.g., unreacted isomerized olefin and hydrogenated olefin (e.g., corresponding saturated hydrocarbons or paraffin by-products); and possibly even some in situ type alkyl substituted phosphorus ligand by-product. Further minor amounts of other additional co-solvent type diluents or additives, if employed in the hydroformylation process, may correspondingly be present in the liquid medium starting materials of this invention. Accordingly, it should be sufficient for the purpose of this invention to understand that whatever compounds are present in the hydroformylation reaction medium of the hydroformylation process from which the organic liquid medium starting material of this invention is derived, may also be correspondingly present in said organic liquid medium starting materials.

Reaction conditions for effecting such hydroformylation processes are conventionally known as seen by the above cited references and may comprise a reaction temperature of from about 45° C. to about 200° C. and pressures ranging from about 1 to 10,000 psia. While such hydroformylation reaction conditions are not critical to the process of this invention, preferably the organic liquid medium starting materials of this invention are those derived from a low pressure hydroformylation process, e.g. one operated at a total gas pressure of hydrogen, carbon monoxide and olefinic unsaturated starting compound of less then about 1500 psia and more preferably less than about 500 psia.

It is to be further understood that while the subject invention is preferably directed to treating an organic liquid medium that has been directly obtained from a hydroformylation process, the organic liquid medium starting materials of this invention also encompass any subsequent organic liquid medium derived from such an initial organic liquid medium so obtained, provided said subsequently derived organic liquid medium also contains at least some amount of each of the four main ingredients defined above i.e., the partially deactivated rhodium - tertiary organophosphine complex catalyst, the free tertiary organophosphine ligand, the aldehyde product, and said higher boiling aldehyde condensation by-products.

As pointed out above, an aqueous solution of 1 to 25 percent by weight of a tertiary alkanolamine can be employed to remove the halide and/or carboxylic acid poisons from the organic liquid starting materials of this invention. Such tertiary alkanolamines include those of the formula

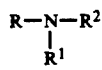

wherein R is a hydroxyalkyl radical containing from 2 to 4 carbon atoms; and wherein $R^1$ and $R^2$ are each individually selected from the group consisting of alkyl radicals containing from 1 to 4 carbon atoms, hydroxyalkyl radicals containing from 2 to 4 carbon atoms, and a phenyl radical. The more preferred tertiary alkanolamines are trialkanolamines (i.e., wherein each R, $R^1$ and $R^2$ group is a hydroxyalkyl radical containing from 2 to 4 carbon atoms). Illustrative tertiary alkanolamines include triethanolamine, triisopropanolamine, tri-sec-butanolamine, diethylethanolamine, dimethylethanolamine, dibutylethanolamine, phenylethylethanolamine, methyldiethanolamine, ethyldiethanolamine, phenyldiethanolamine, dimethylisopropanolamine, diisopropanolethanolamine, and the like. Of course, the aqueous tertiary alkanolamine solution employable herein may contain a mixture of two or more of such tertiary alkanolamines, if desired. The most preferred tertiary alkanolamine is triethanolamine.

Thus the novel process of this invention consists essentially of mixing the organic liquid starting material as defined above, with the aqueous solution of tertiary alkanolamine, allowing the mixture thereof to settle into two distinct phases and separating the aqueous (bottom) phase which contains the correspondingly produced water soluble salts of said tertiary alkanolamine and said halide and/or carboxylic acid posions, from the organic (top) phase containing the reactivated solubilized rhodium-tertiary organophosphine complex catalyst and the remainder of the organic liquid medium starting material, e.g. the aldehyde product, the free organophosphine ligand, and the higher boiling aldehyde condensation by-products, followed by washing said organic phase so obtained, to further remove any minor amounts of said produced amounts of the tertiary alkanolamine and/or said produced amine salts, that might have been left behind in the organic liquid medium, prior to reusing the obtained solubilized reactivated rhodium-tertiary organophosphine complex catalyst solution in a restarted or new hydroformylation process.

More particularly, the process of this invention is conducted under non-hydroformylation conditions, i.e., in the essential absence of syn gas ($CO+H_2$), and Step (1) of the process is accomplished by merely mixing the aqueous solution of tertiary alkanolamine with the desired organic liquid medium starting material to produce water-soluble salts of said tertiary alkanolamine and whatever halide and/or carboxylic acid Poison is present in said organic liquid medium starting material. Said mixing of the aqueous solution of tertiary alkanolamine with the organic liquid medium starting material can be carried out in any conventional fashion using any suitable equipment and technique, the preferred result merely being a thorough inclusion of the tertiary alkanolamine in the organic liquid medium so as to produce as much of such water-soluble salt products between said tertiary alkanolamine and halide and/or carboxylic acid poisons as possible. In general merely adding the aqueous solution of tertiary alkanolamine to the organic liquid medium and gently agitating or stirring the solutions should be sufficient to accomplish the desired result. Of course too vigorous a mixing is to be avoided since such might contribute to undesirable emulsion formation, which in turn can prevent and/or unduly adversely hinder the desired phase separation of the aqueous and organic phases. In general Step (1) of the process of this invention may be carried out at liquid temperatures ranging from about 10° C. to about 150° C., and more preferably from about 40° C. to about 100° C., while temperatures ranging from about 45° C. to about 75° C. are most preferred. It is further generally preferred to carry out said treatment at atmospheric (ambient) pressure, although higher or lower pressures may be employed if desired. It should be noted that the higher the temperature the greater the chance for causing undesirable increased aldehyde condensation by-product formation during Step (1), while the lower the temperature the greater the risk of undesirable emulsion formation due to increased solubility between the aldehyde and water. Accordingly if it is found that emulsion formation is beginning to occur during Step (1) of the process of this invention, such may be abated by adding more aldehyde to the organic liquid medium starting material. Of course it is obvious that the contact time of the aqueous tertiary alkanolamine solution and the organic liquid medium involved may vary from a matter of minutes to a few hours. Experience will determine the most preferred temperature and contact time.

The process of this invention is carried out under non-hydroformylation conditions, which is to say that it is carried out in the essential absence of syn gas ($CO+H_2$), thus preventing any adverse simultaneous hydroformylation or other undesirable side reactions. Preferably the process of this invention is carried out under a nitrogen atmosphere, although mixtures of nitrogen and any other gas (except syn gas) may be employed provided that such does not unduly adversely affect the desired purpose of this invention.

The tertiary alkanolamine concentration in the aqueous solution employable in Step (1) of the process of this invention need only be that minimum amount necessary to help achieve at least some improvement in the hydroformylation activity of the partially deactivated rhodium-tertiary organophosphine complex catalyst in the organic liquid medium starting material. Preferably the amount of tertiary alkanolamine employed will be sufficient to neutralize (form a salt with) at least 10 percent, and more preferably theoretically all, of the halide and/or carboxylic acid poisons present in the organic liquid medium starting material. In general, aqueous solutions containing from about 1 to 25 percent by weight of the tertiary alkanolamine should be sufficient for most purposes with aqueous solutions containing from about 4 to about 15 percent by weight of the tertiary alkanolamine being preferred.

While from about 0.5 to 20 volume equivalents of said organic liquid medium starting material per volume equivalent of the aqueous solution of tertiary alkanolamine may be used, in general, in Step (1) of the process of this invention, it is preferred to employ organic to aqueous liquid ratios of from about 1 to about 5 volume equivalents, and more preferably from about 1 to about 3 volume equivalents, of said organic liguid medium starting material per volume equivalent of the aqueous solution of tertiary alkanolamine.

Step (2) of the process of this invention merely consists of allowing the resultant solution mixture of Step (1) to settle into two distinct liquid phases, i.e. an organic (top) phase containing the catalyst, aldehyde and other non-water soluble ingredients of the organic liquid medium starting material, and an aqueous (bottom) phase containing the produced water-soluble salts of tertiary alkanolamine and the halide and/or carboxylic acid poisons that were present in the organic liquid medium starting material. The settling time necessary for said phase separation has no effect on the activity of the catalyst and is dictated only by the ease with which the organic and aqueous phases undergo such separation. Preferably such separation should be completed within a day's time and more preferably within a matter of a few hours or only minutes.

Step (3) of the process of this invention merely consists of the physical separation of said aqueous and organic phases produced by Steps (1) and (2), and such separation may be accomplished by any suitable conventional means, such as by draining off the bottom layer, or decanting off the top layer, and the like.

Step (4) of the process of this invention merely consists essentially of washing the obtained resultant organic phase of Step (3) with water, so as to remove any residual amounts of tertiary alkanolamine and/or said produced amine salts, that might have been left behind in the organic phase. Said water wash may be carried out in any conventional manner and suitable fashion. Ordinary tap water may be employed although deionized or distilled water or steam condensate is preferred. The same general type and preferred treatment conditions as employed in above Steps (1) (2) and (3) may be used in Step (4), e.g. the treatment being carried out under non-hydroformylation conditions and under an inert atmosphere and preferably using an organic liquid to water volume ratio of about 1 to 5, and more preferably about 1 to 3, volume equivalents of the organic liquid per volume equivalent of water. Moreover said water wash is preferably conducted under atmospheric (ambient) pressure and at a liquid temperature of about 40° C. to about 100° C. and more preferably from about 45° C. to abut 75° C. Thus it may be preferred to heat the obtained organic medium following the aqueous tertiary alkanolamine treatment in order to achieve such recommended temperatures for said water wash. Alternatively, hot water or steam condensate could be used for the wash. The recovery of the organic phase of said water wash (Step 4) containing a solubilized rhodium-tertiary organophosphine complex hydroformylation catalyst that is more catalytically active than the initial partially deactivated rhodium-tertiary organophosphine complex hydroformylation catalyst starting material of the process of this invention may be accomplished in the same manner as described above for the aqueous tertiary alkanolamine treatment, see above Steps (2) and (3). For instance, following a suitable mixing period the aqueous and organic layers are allowed to phase separate (settle) and the two liquid layers removed from each other by draining off the bottom phase and/or decantating off the top phase.

A uniquely beneficial aspect of the present invention is that repeated water washings, such as is common place when following a conventional aqueous alkaline wash to remove acids from a medium, are not required by the process of this invention. Tertiary alkanolamines and especially triethanolamine are far milder catalysts for the formation of higher boiling aldehyde condensation by-products than alkali compounds and thus the removal of such minor amounts of residual tertiary alkanolamine and/or salts that might be left behind in the organic medium obtained after the initial aqueous tertiary alkanolamine treatment is not nearly as important as compared to a situation wherein an aqueous alkali wash treatment might be carried out. Thus it is recommended that Step (4) of the process of this invention consist of only a single such water wash. Repeated water washings, while possible, are considered unnecessary and are not recommended. Indeed such repeated water washings in the practice of this invention may serve only to increase the risk of undesirable emulsion formation.

Thus it should be clear that while the selection of the optimum conditions of this invention to achieve the best results will be dependent upon one's experience in the utilization of the subject invention, in view of the disclosure and examples of this specification, only a certain measure of routine experimentation should be necessary in order to ascertain those conditions which are optimum for a given situation. Moreover, it should also be clear that one of the beneficial factors involved in this invention as employed herein is the wide processing latitude that one has in selecting the proper combination of conditions that will be most useful in obtaining or at least best approaching a particular desired result or need.

The improved regenerated hydroformylation catalytic activity of a rhodium complex catalyst obtained according to this invention, may be determined by any suitable method such as e.g., by measuring the rates of reaction of the partially deactivated rhodium complex catalyst in the liquid medium starting material of Step (1) and the reactivated rhodium complex catalyst obtained according to this invention as compared the activity of a fresh rhodium complex catalyst (i.e., undeactivated catalyst) employed in the same manner. This effect may be easily determined by carrying out the hydroformylation reactions and by continuously monitoring the rate of hydroformylation. The difference in hydroformylation rate (or difference in catalyst activity) may then be observed in a convenient laboratory time frame, such as in terms of gram-moles per liter-hour of aldehyde product produced.

Thus the process of this invention provides an excellent means for improving the hydroformylation catalytic activity of a solubilized rhodium-tertiary organophosphine complex hydroformylation catalyst which has become partially deactivated as a result of halide and/or carboxylic acid poisoning, e.g., by treating all or part of the hydroformylation reaction medium of such a process or all or part of the catalyst complex containing liquid recycle medium of such process.

For instance a particularly preferred and beneficial aspect of this invention may comprise merely stopping a rhodium-tertiary organophosphine catalyzed continuous hydroformylation reaction and treating the hydroformylation reaction medium derived therefrom according to the process of this invention while said reaction medium remains in the hydroformylation reactor, to obtain the desired reactivated hydroformylation catalyst that is more catalytically active than the partially deactivated halide and/or carboxylic acid poisoned catalyst contained in said starting reaction medium. The hydroformylation reaction can obviously be stopped by any convenient method, e.g., by merely stopping the feed of the reactant gases (olefin, carbon monoxide and hydrogen) to the reaction vessel, allowing the residual reactants contained therein to react to completion, and shutting down the reaction being conducted in the reaction vessel. The recycle lines of the continuous reaction system can then be cleared in any conventional manner and the derived hydroformylation medium treated according to the process of this invention. If a reactor or reaction vessel is essentially completely full of the liquid aldehyde product containing hydroformylation reaction medium, it may be necessary to first reduce the volume of the organic liquid medium in the reactor by removing some of the aldehyde product in order to accommodate the liquid volume of the aqueous solution of tertiary alkanolamine employed in the process of this invention. Such may be accomplished by stripping out whatever amount of aldehyde is desired from the reactor after the feed gases have been shut down. When done, however, it is recommended to leave a substantial aldehyde concentration in the medium. For instance it is recommended to avoid concentrations of said organic liquid hydroformylation reaction mediums which would result in aldehyde concentrations of below 30 percent, since experience has indicated that as the aldehyde concentration in the organic liquid medium starting material decreases the ease of phase separation between the organic and aqueous layers also decreases, while the risk of emulsion formation increases. In general, concentrations of the organic liquid hydroformylation medium in a full reactor to about 70 percent should be suitable for most instances. Of course if the reactor vessel is not essentially full of the liquid aldehyde product containing hydroformylation reaction medium and can directly accommodate a suitable amount of the aqueous tertiary alkanolamine, it may not be necessary to concentrate the hydroformylation reaction medium at all. The aqueous solution of tertiary alkanolamine which is preferably made up in a separate vessel and analyzed to insure avoiding such possible contaminates as iron, halide, alkali metal and primary and secondary alkanolamines may be added to the organic liquid medium of the reactor in any conventional suitable manner such as by pressuring the aqueous tertiary alkanolamine solution into the reactor from a suitable pressurized bomb. Following the addition of the aqueous solution of tertiary alkanolamine the reactor solutions are gently agitated to provide sufficient mixing of the two phases to achieve one theoretical stage. Reaction of chlororhodium complexes with the aqueous solution is fast and may be complete almost as soon as contact is made between the aqueous and organic phases. Agitating the reaction mixture for about one hour should be adequate for most purposes. After mixing, the mixture is allowed to separate (e.g., for a period of about four hours) into two distinct liquid phases. The aqueous phase will settle to the bottom of the reactor vessels and may be drained from any suitable accessible low point in the reaction process. As the aqueous layer is removed it should be retained in the unlikely event that it contains a higher than expected rhodium concentration. It is recommended that the solution be visually monitored to determine when the aqueous layer has been completely removed from the reactor vessels and the organic solution begins to drain. Liquid level detectors may also be useful to determine when the interface is approaching the drain valve, but close visual monotoring is preferred. In laboratory experiments, the aqueous layer has a cloudy, milky white appearance, while the reactivated organic catalyst solution is a clear brown. In order to remove residual portions of the tertiary alkanolamine and the amine salts from the reactivated catalyst containing organic solution, said organic solution may be washed with water as described above, in the same reactor vessels. Before the entire aqueous phase of said wash treatment is removed from the reactor, it is recommended to measure a sample of same for rhodium content in order to prevent an inadvertent loss of rhodium due to inadequate settling time. Minor amounts of rhodium in the aqueous phases of the recovered tertiary alkanolamine and water washes may be reclaime by extracting the rhodium therefrom with the addition of an aldehyde such as butyraldehyde.

No special precautions need be considered for re-startup of the continuous hydroformylation reaction using the obtain reactivated catalyst solution in the reactor. Possible further minor amounts of water and- /or tertiary alkanolamine left in the reactor vessels after the process of this invention are of no major concern as noted above. Such will be gradually stripped out of the restarted hydroformylation via an aldehyde product vaporizer.

Unlike some prior art reactivation procedures that require the addition of make-up quantities of active rhodium catalyst, solvent and/or triarylphosphine before reutilizing their treated catalyst, the subject inventive process is unique in that since the treatment of this invention can be carried out in the same reaction vessel of the hydroformylation reaction one need only turn back on the feed of olefinic compound, hydrogen and carbon monoxide to the treated hydroformylation reaction medium of this invention and restart the continuous hydroformylation reaction without the need of adding additional reaction medium components before restarting the reaction. Moreover, if one is using more than one reaction vessel in conjunction with the continuous hydroformylation reaction one need not shut off the reaction being conducted in every reaction vessel, but only the reaction that is being conducted in that reaction vessel in which the derived hydroformylation medium is to be treated. Alternatively it is to be understood that if desired, one could remove the entire hydroformylation reaction medium to be treated according to this invention from the reaction vessel of the hydroformylation reaction to a different vessel and then treat all or a proportionate part of said medium in said different vessel as desired. Such an optional procedure allows one to employ the empty hydroformylation reaction vessel for any other type of purpose such as for hydroformylating a different olefinic compound than employed in the initial hydroformylation reaction from which the medium to be treated has been derived. This would allow one to store the medium to be treated or the medium so treated until it is desired to be reused. Alternatively, yet another preferred aspect and benefit of this invention involves treating all or part of the liquid catalyst containing recycle medium of a such a continuous hydroformylation process with the aqueous solution of tertiary alkanolamine and returning the thus treated catalyst containing recycle medium to the reaction medium in the reactor of the continuous hydroformylation process. Such may be accomplished by any suitable method, e.g., drawing off a part of the recycle medium to an appropriate container treating same and returning the treated medium, without any need for stopping or shutting down the continuous hydroformylation. Of course likewise a portion of the hydroformylation reaction medium itself may be withdrawn from the reactor, and also so treated and returned to the reactor in the same fashion, if desired, without stopping or shutting down the continuous hydroformylation as noted above.

Further in addition to being readily returnable to or used as the reaction medium of the same hydroformylation process from whence the partially deactivated rhodium - tertiary organophosphine complex catalyst starting materials of Step (1) may be derived, the reactivated rhodium - tertiary organophosphine complex product of this invention, if desired, may be useful as the catalytic starting material or as a catalytic booster for any different conventional hydroformylation process.

The following examples are illustrative of the present invention and are not to be regarded as limitative. It is to be understood that all parts, percentages and proportions referred to herein and in the appended claims are by weight unless otherwise indicated.

EXAMPLE 1

A chloride poisoned rhodium-triphenyl-phosphine hydroformylation complex catalyst solution was prepared by mixing in a nitrogen purged bottle, about 0.2393 grams of hydridocarbonylrhodium triphenylphosphineacetyl acetonate and about 0.5592 grams of hydridorhodiumtetrakis(triphenylphosphine), about 5.5 grams of free triphenylphosphine, about 20 grams of butyraldehyde, about 24.05 grams of Texanol ® (a mixture of butyraldehyde trimers) and about 41 micro liters ($\mu$l) of concentrated HCl. The bottle was then purged with syn gas pressurized to about 60 psig and heated at 70° C. for about 30 minutes. The prepared catalyst composition contained about 1000 ppm of rhodium, about 11.3 percent by weight of triphenylphosphine ligand, about 35 percent by weight of butyraldehyde and about 53.7 percent by weight of Texanol ® and other higher boilers.

A portion (about 15 ml) of the rhodium-triphenylphosphine complex catalyst solution so prepared was then charged to a glass mini-reactor and the rate of hydroformylation obtained in terms of gram-moles per liter-hour of produced aldehyde upon hydroformylating propylene to butyraldehyde at about 100° C. under about 95 psig of carbon monoxide, hydrogen and propylene in a 1:1:1 mole ratio was determined. The catalyst activity was found to be only about 26 percent as compared to the known activity obtainable by using fresh (undeactivated) rhodium-triphenylphosphine complex hydroformylation catalyst under essentially the same conditions.

About 25 grams of the remaining chloride poisoned rhodium-triphenylphosphine complex catalyst solution so prepared as described above was mixed with about 10 grams of an aqueous solution containing about 15 percent by weight of triethanolamine and the solution gently stirred for about 10 minutes at about 100° C. The solution mixture was then allowed to settle into two distinct aqueous and organic phases (which was rapidly accomplished in about 5 minutes) and said two liquid phase layers separated by decantation. The organic phase solution so obtained was then washed only once with distilled water, employing essentially same mixing, settling and separation conditions as employed in said previous aqueous-triethanolamine treatment.

About 15 ml. of the organic solubilized rhodium-triphenylphosphine complex catalyst organic solution obtained after said water wash treatment was then charged to a glass mini-reactor and the rate of hydroformylation obtained upon hydroformylating propylene under the same conditions as described above was determined. The catalyst activity was found to have improved to about 79 percent as compared to the known activity obtainable by using a fresh (undeactivated) rhodium-triphenylphosphine complex hydroformylation catalyst under essentially the same conditions.

EXAMPLE 2

A chloride poisoned rhodium-triphenylphosphine hydroformylation complex catalyst solution was prepared by mixing in a nitrogen purged bottle, about 0.0308 grams of hydridorhodiumtetrakis(triphenylphosphine), about 6 grams of free triphenylphosphine, about 49 grams of butyraldehyde, and about 2.2 micro liters ($\mu$l) of concentrated HCl. The bottle was then purged with syn gas pressurized to about 60 psig and heated at 70° C. for about 30 minutes. The prepared catalyst composition contained about 50 ppm of rhodium, about 9.5 percent by weight of triphenylphosphine ligand, and about 90.5 percent by weight of butyraldehyde and other higher boilers.

A portion (about 15 ml) of the rhodium-triphenylphosphine complex catalyst solution so prepared was then charged to a glass mini-reactor and the rate of hydroformylation obtained in terms of gram-moles per liter-hour of produced aldehyde upon hydroformylating propylene to butyraldehyde at about 100° C. under about 95 psig of carbon monoxide, hydrogen and propylene in a 1:1:1 mole ratio was determined. The catalyst activity was found to be only about 53 percent as compared to the known activity obtainable by using fresh (undeactivated) rhodium-triphenylphosphine complex hydroformylation catalyst under essentially the same conditions.

About 25 grams of the remaining produced chloride poisoned rhodium-triphenylphosphine complex catalyst solution so prepared as described above was mixed with about 10 grams of an aqueous solution containing about 3 percent by weight of triethanolamine and the solution gently stirred for about 10 minutes at about 40° C. The solution mixture was then allowed to settle into two distinct aqueous and organic (phases which was rapidly accomplished in about 5 minutes) and said two liquid phase layers separated by decantation. The organic phase solution so obtained was then washed with distilled water, employing essentially same mixing, settling and separation conditions as employed in said previous aqueous-triethanolamine treatment.

About 15 ml. of the solubilized rhodium-triphenylphosphine complex catalyst organic solution obtained after said water wash treatment was then charged to a glass mini-reactor and the rate of hydroformylation obtained upon hydroformylating propylene under the same conditions as described above was determined. The catalyst activity was found to have improved to about 83 percent as compared to the known activity obtainable by using a fresh (undeactivated) rhodium-triphenylphosphine complex hydroformylation catalyst under essentially the same conditions.

EXAMPLE 3

A rhodium-[2,2'-bis(diphenylphosphino-methyl)-1,1'-dibenzyl]hydroformylation complex catalyst solution was prepared by mixing in a nitrogen purged bottle about 0.0549 grams of rhodiumdicarbonylacetyl-acetonate and about 0.75 grams of free [2,2'-bis(diphenylphosphino-methyl)-1,1'-dibenzyl]]ligand, about 52.5 grams of butyraldehyde, and about 21.7 grams of Texanol ®. The prepared catalyst composition contained about 301 ppm of rhodium, about 1.0 percent by weight of [2,2'-bis(diphenylphosphinomethyl)-1,1'-dibenzyl]ligand, about 70 percent by weight of butyraldehyde and about 29 percent by weight of Texanol ®. About 25 grams of this solution was removed to a second bottle and a portion (about 15 ml) of said rhodium-[2,2'-bis(diphenylphosphinomethyl)-1,1'- dibenzyl] complex catalyst solution so prepared was then charged to a glass mini-reactor to establish a 100 percent activity level for the rate of hydroformylation obtained in terms of gram-moles per liter-hour of produced aldehyde upon hydroformylating propylene to butyraldehyde at about 100° C. under about 95 psig of carbon monoxide, hydrogen and propylene in a 1:1:1 mole ratio using said fresh (undeactivated) catalyst.

About 12 micro liters (μl) of concentrated HCl was then added to the remaining 50 grams of the initially prepared rhodium complex catalyst solution to poison same and the bottle purged with syn gas, pressurized to about 60 psig and then heated at 70° C. for about 30 minutes. A portion (about 15 ml.) of this chloride poisoned rhodium complex catalyst solution so prepared was then charged to a glass mini-reactor and the rate of hydroformylation obtained in terms of gram-moles per liter-hour of produced aldehyde upon hydroformylating propylene to butyraldehyde at about 100° C. under about 95 psig of carbon monoxide, hydrogen and propylene in a 1:1:1 mole ratio was determined. Said catalyst activity was found to be only about 54 percent as compared to the earlier activity obtained as described above for said fresh (undeactivated or non-chloride poisoned) rhodium complex catalyst under the same conditions.

About 25 grams of the remaining produced chloride poisoned rhodium-[2,2'-bis(diphenyl-phosphinomethyl)-1,1'-dibenzyl] complex catalyst solution so prepared as described above was mixed with about 10 grams of an aqueous solution containing about 5 percent by weight of triethanolamine and the solution gently stirred for about 10 minutes at about 60° C. The solution mixture was then allowed to settle into two distinct aqueous and organic phases (which was rapidly accomplished in about 5 minutes) and said two liquid phase layers separated by decantation. The organic phase solution so obtained was then washed only once with distilled water, using essentially the same mixing, settling and separation conditions as employed in said previous aqueous-triethanolamine treatment.

About 15 ml. of the solubilized rhodium-[2,2'-bis(diphenylphosphinomethyl)-1,1'-dibenzyl]complex catalyst organic solution obtained after said water wash treatment was then charged to a glass mini-reactor and the rate of hydroformylation obtained upon hydroformylating propylene under the same conditions as described above was determined. The catalyst activity was found to have improved to about 98 percent as compared to the earlier activity obtained as described above for said fresh (undeactivated or non-chloride poisoned) rhodium complex catalyst under the same conditions.

EXAMPLE 4

A rhodium-cyclohexyldiphenylphosphine hydroformylation complex catalyst solution was prepared by mixing in a nitrogen purged bottle about 0.549 grams of rhodiumdicarbonylacetylacetonate and about 4.5 grams of free cyclohexyldiphenylphosphine ligand, about 52.5 grams of butyraldehyde, and about 18 grams of Texanol ®. The prepared catalyst composition contained about 315 ppm of rhodium, about 6 percent by weight of cyclohexyldiphenylphosphine ligand, about 70 percent by weight of butyraldehyde and about 24 percent by weight of Texanol ®. About 25 grams of this solution was removed to a second bottle and a portion (about 15 ml) of said removed rhodium-cyclohexyldiphenyl-phosphine ligand, complex catalyst solution so prepared was then charged to a glass mini-reactor to establish a 100 percent activity level for the rate of hydroformylation obtained in terms of gram-moles per liter-hour of produced aldehyde upon hydroformylating propylene to butyraldehyde at about 100° C. under about 95 psig of carbon monoxide, hydrogen and propylene in a 1:1:1 mole ratio using said fresh (undeactivated) catalyst.

About 12 micro liters (μl) of concentrated HCl was then added to the remaining 50 grams of the initially Prepared rhodium complex catalyst solution to poison same and the bottle purged with syn gas, pressurized to about 60 psig and then heated at 70° C. for about 30 minutes. A portion (about 15 ml.) of the chloride poisoned rhodium complex catalyst solution so prepared was then charged to a glass mini-reactor and the rate of hydroformylation obtained in terms of gram-moles per liter-hour of produced aldehyde upon hydroformylating propylene to butyraldehyde at about 100° C. under about 95 psig of carbon monoxide, hydrogen and propylene in a 1:1:1 mole ratio was determined. Said catalyst activity was found to be only about 42 percent as compared to the earlier activity obtained as described above for said fresh (undeactivated or non-chloride poisoned) rhodium complex catalyst under the same conditions.

About 25 grams of the remaining produced chloride poisoned rhodium-cyclohexyldiphenyl-phosphine complex catalyst solution so prepared was mixed with about 10 grams of an aqueous solution containing about 5 percent by weight of triethanolamine and the solution gently stirred for about 10 minutes at about 60° C. The solution mixture was then allowed to settle into two distinct aqueous and organic phases (which was rapidly accomplished in about 5 minutes) and said two liquid phase layers separated by decantation. The organic phase solution so obtained was then washed only once with distilled water, using essentially the same mixing, settling and separation conditions as employed in said previous aqueous-triethanolamine treatment.

About 15 ml. of the solubilized rhodium-cyclohexyldiphenylphosphine complex catalyst organic solution obtained after said water wash treatment was then charged to a glass mini-reactor and the rate of hydroformylation obtained upon hydroformylating propylene under the same conditions as described above was determined. The catalyst activity was found to have improved to about 86 percent as compared to the earlier activity obtained as described above for said fresh (undeactivated or non-chloride poisoned) rhodium complex catalyst under the same conditions.

EXAMPLE 5

An organic liquid medium starting material was derived from a commercial continuous gaseous hydroformylation reaction involving the use of two reactors and the hydroformylation of propylene to butyraldehyde by reacting propylene, carbon monoxide and hydrogen in the presence of a hydroformylation reaction medium in said reactors, by shutting off the reactant feed gases, stopping the hydroformylation reaction and stripping essentially all (more than 99.5 percent) of the reactant gases from the reaction vessels and cycle lines of the system. The hydroformylation reaction mediums contained an average of about 75 percent by weight of butyraldehyde Products, about 14 percent by weight of higher boiling aldehyde condensation by-products and the higher boilers, about 11 percent by weight of free triphenylphosphine ligand, and a solubilized rhodium complex hydroformylation catalyst consisting essentially of rhodium complexed with carbon monoxide and triphenylphosphine in an amount sufficient to provide about 340 ppm rhodium. The average catalytic activity of such hydroformylation reaction mediums had deactivated to about 50 percent of fresh catalyst, said decline in activity being primarily attributable to an inadvertent build-up of chloride poisoning, presumably sourced from the propylene feed stocks. At least about 40 percent of such catalytic activity decline was considered attributable to the presence of about 50 ppm chloride (calculated as free chlorine) which considered to be causing about 40 percent of the rhodium in the catalyst system of the hydroformylation reaction mediums to be present as an inactive chlororhodium complex. Moreover, after storage for six weeks, it was noticed that the catalytic activity of said chloride poisoned hydroformylation reaction mediums had experienced a further decline (i.e. down from the above mentioned 50 percent of fresh rhodium activity) to about 20 percent of fresh rhodium activity. This further decline in activity is presumed to have been caused by the buildup of additional heavy acid inhibitors, such as might occur as a result of oxidation of the aldehyde and/or higher boiling aldehyde condensation by-products, during said storage of the hydroformylation mediums.

The hydroformylation reaction mediums in said reactors containing the obtained poisoned rhodium-triphenylphosphine complex catalysts having a catalytic activity of only about 20 percent of fresh rhodium catalyst as discussed above were stripped down to remove about 30 percent by weight of aldehyde and lighter boiling components, e.g., propylene, propane, etc. During this period the two reactors were cooled to about 70° C. A mixture of a 5 percent aqueous triethanolamine solution in an amount equal to about 47 percent by weight (about 38 percent by volume) of the total weight of said stripped hydroformylation reaction mediums was prepared in a separate catalyst mix tank and heated to about 60° C. The aqueous triethanolamine was then proportionately (one half to each reactor) transferred (pressurized) to the two reactors over a period of about 12 hours and after the aqueous solution had been transferred, each reactor was agitated for one hour. The mixed solution in one reactor was allowed to settle (separate) into two distinct aqueous and organic phases over a period of 4 hours, while the mixed solution in the second reactor was allowed to settle (separate) into two distinct aqueous and organic phases over a period of 2 hours. The aqueous phases were then drained from the hydroformylation reaction process system via outlet valves in discharge lines below the reactors. After said triethanolamine treatment and removal of the aqueous phase, the first reactor was heated back up to about 100° C. to prepare for a water wash, while the temperature of the second reactor was maintained at about 70° C. Clean water (i.e., steam condensate) in an amount equal to about 38 percent by weight of the weight of the rhodium-triphenylphosphine complex catalyst containing organic liquid phase composition remaining in each reactor after said triethanol amine treatment was transferred (pressurized) to each reactor over about a 6 hour transfer time. Each reactor was then agitated for one hour and the mixed solutions allowed to settle into two distinct aqueous and organic phases over 4 hours. The aqueous phases in both reactors were then drained from the hydroformylation reaction process system in the same manner as described above.

After the removal of said aqueous phases, the reactors were then heated to about 80° C.-85° C. and the propylene hydroformylation restarted by feeding the propylene and syn gas reactants to said reactors in the normal fashion for commercial production of butyraldehyde. The activity of the rhodium-triphenylphosphine complex catalyst of said treated hydroformylation reaction mediums was found to have improved to about 63-65% of fresh rhodium catalyst immediately upon said restartup of the hydroformylation process. Moreover the chloride content in the hydroformylation reaction mediums was found to have been reduced from about 50 ppm to about 10 ppm.

Various modifications and variations of this invention will be obvious to a worker skilled in the art and it is to be understood that such modifications and variations are to be included within the purview of this application and the spirit and scope of the appended claims.

What is claimed is:

1. A process for improving the catalytic activity of a solubilized rhodium tertiary organophosphine complex hydroformylation catalyst which has become partially deactivated due to halide and/or carboxylic acid poisoning, said process consisting essentially of
   (1) mixing under non-hydroformylation conditions, an organic liquid medium containing said solubilized partially deactivated rhodium-tertiary organophosphine complex catalyst, with an aqueous solution containing from about 1 to about 25 percent by weight of a tertiary alkanolamine having the formula

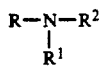

wherein R represents a hydroxyalkyl radical having from 2 to 4 carbon atoms; wherein $R^1$ and $R^2$ each individually represent a radical selected from the group consisting of alkyl radicals having from 1 to 4 carbon atoms, hydroxyalkyl radicals having from 2 to 4 carbon atoms, and a phenyl radical, to form a water-soluble salt between said tertiary alkanolamine and said halide and/or carboxylic acid;
   (2) allowing the resulting mixture to settle into two distinct liquid phases;
   (3) separating the aqueous phase which contains said salt from the organic phase containing the solubilized rhodium-tertiary organophosphine complex hydroformylation catalyst resulting from steps (1) and (2); and;
   (4) washing the separated organic phase obtained by step (3) with water, and recovering a solubilized rhodium-tertiary organophosphine complex hydroformylation catalyst that is more catalytically active than said Partially deactivated rhodium-tertiary organophosphine complex hydroformylation catalyst starting material.

2. A process as defined in claim 1, wherein $R^1$ and $R^2$ each represent a hydroxyalkyl radical having from 2 to 4 carbon atoms.

3. A process as defined in claim 1, wherein the tertiary alkanolamine is triethanolamine.

4. A process as defined in claim 3, wherein the solubilized partially deactivated catalyst has become at least 25 percent deactivated as a result of said halide and/or carboxylic acid poisoning.

5. A process as defined in claim 3, wherein the halide is chlorine.

6. A process as defined in claim 4, wherein the organic liquid medium starting material of step (1) comprises all or part of the hydroformylation reaction medium of a continuous non-aqueous hydroformylation process.

7. A process as defined in claim 6, wherein Step (1) is carried out in the hydroformylation reactor of said hydroformylation process.

8. A process as defined in claim 4, wherein the organic liquid medium starting material of Step (1) comprises all or a part of the liquid catalyst containing recycle medium of a continuous non-aqueous hydroformylation process.

9. A process as defined in claim 6, wherein said organic liquid medium starting material contains a rhodium-triphenylphosphine complex catalyst and at least about 30 percent by weight of aldehyde.

10. A process as defined in claim 9, wherein the aldehyde is a mixture of n-butyraldehyde and isobutyraldehyde.

11. A process as defined in claim 4, wherein Step (1) is conducted at a temperature of about 45° C. to about 75° C.

12. A process as defined in claim 11, wherein Step (4) consists essentially of a single agueous wash.

13. A process as defined in claim 7, wherein said organic liquid medium contains at least about 30 percent by weight of aldehyde.

14. A process as defined in claim 13, wherein Step (1) is conducted at a temperature of about 45° C. to about 75° C.

15. A process as defined in claim 14, wherein Step (4) consists essentially of a single aqueous wash.

* * * * *